United States Patent [19]
Mettes

[11] Patent Number: 5,225,065
[45] Date of Patent: Jul. 6, 1993

[54] EPOXY-LESS LOW-LEVEL MOISTURE MEASUREMENT SYSTEM AND METHOD

[75] Inventor: Jacob Mettes, Doylestown, Pa.

[73] Assignee: Meeco, Inc., Warrington, Pa.

[21] Appl. No.: 592,348

[22] Filed: Oct. 3, 1990

[51] Int. Cl.$^5$ .......................................... G01N 27/26
[52] U.S. Cl. ................. 204/430; 204/153.22; 204/409; 204/400
[58] Field of Search ............. 204/153.22, 400, 409, 204/430, 286, 297 R

[56] References Cited

U.S. PATENT DOCUMENTS

| | | | |
|---|---|---|---|
| 3,223,609 | 12/1965 | Reeds, Jr. ............................ | 204/430 |
| 3,696,007 | 10/1972 | Bennett et al. .................. | 204/153.22 |
| 4,589,971 | 5/1986 | Mayeaux ............................ | 204/409 |
| 4,773,275 | 9/1988 | Kalinoski ............................ | 204/400 |
| 4,800,000 | 1/1989 | Zatko et al. ........................ | 204/409 |
| 4,842,709 | 6/1989 | Mayeaux ........................ | 204/153.22 |

OTHER PUBLICATIONS

Ceramaseal, a Divison of Ceramx, "Ceramic to Metal Component Catalog" (catalog 8710 Rev. A 1989), p. A-2.

Supeko, a Rohm and Haas Company, "Chromatography Products" (catalog 27, 1989), pp. 110, 111.

Primary Examiner—John Niebling
Assistant Examiner—Bruce F. Bell
Attorney, Agent, or Firm—Ratner and Prestia

[57] ABSTRACT

Low-level water concentrations are measured in gases by an electrolytic cell in which contaminating epoxy components present in conventional electrolytic cells have been eliminated. A metal-glass connection seal mechanically fixes the glass detection unit within the metal housing of the cell and provides a leak-proof barrier between the entrance and exit of the cell. Electrical insulator assemblies serve as insulators for the cell electrodes and also provide a leak-proof barrier where the electrical connections penetrate the metal housing of the cell.

13 Claims, 4 Drawing Sheets

EPOXY-LESS LOW-LEVEL MOISTURE MEASUREMENT SYSTEM AND METHOD

TECHNICAL FIELD

This invention relates to an electrolytic method and device for measuring low-level water concentrations in gases. More particularly, the invention concerns an improved measurement device, which eliminates the epoxy components of conventional electrolytic cells, and an improved method for detecting concentrations of water as low as a few parts per billion by volume within a short response time using the improved device.

BACKGROUND OF THE INVENTION

In many industrial processes, the water concentration of flowing gas streams must be measured and analyzed with a high degree of speed and accuracy. Such measurement and analysis is required because the water concentration is often critical to the quality of the product produced. Consequently, many complex and sophisticated devices are available for measuring water in gases.

These devices typically incorporate an electrolytic cell. The gas to be measured flows through the cell with a known flow rate. The water concentration of the gas is determined by absorbing the water from the gas, using a hygroscopic film, and electrolyzing the water absorbed in that film. Once equilibrium is achieved, the number of molecules electrolyzed per second, measured as the electrolysis current, is proportional to the number of water molecules entering the cell with the gas each second.

An example of a conventional electrolytic cell is described in U.S. Pat. No. 4,800,000 to D. A. Zatko, incorporated herein by reference. All of the known devices use a plastic, typically an epoxy, filler to mechanically fix the detection unit within the cell. The epoxy also serves as an electrical insulator for the electrodes and as a leak-tight barrier between the entrance and exit of the detection unit (the hollow glass tube) of the cell, so that the sample gas will flow only through and not around the detection unit. Finally, the epoxy provides a leak-tight barrier where the electrical connections penetrate through the metal housing of the cell.

As a result, the plastic packing material is present in the vicinity of both the entrance and exit of the sensing device. These materials are known to be relatively porous and to exchange water with the gas stream. It is known that the absorption and emission properties of materials such as plastics form an obstacle to reaching low water concentrations and fast response times in high purity gas systems.

The use of an epoxy potting compound in the conventional electrolytic cells causes many problems. First, a good bond between the epoxy and the metal wall of the cell housing, on one hand, and between the epoxy and the glass tube, on the other hand, must be assured.

Second, epoxy requires a long curing time, which might be as long as one week at room temperature. If insufficient time is allotted to chemically cure the epoxy, the epoxy will retain moisture. Such retention becomes critical when low moisture level performance tests are attempted just after the cell is manufactured.

Another problem is the disparate thermal coefficient of expansion between the epoxy and both metal and glass. Incompatible expansion consequent upon temperature changes which occur during operation of the cell may cause leakage and cracking of the glass tube.

Moreover, the epoxy material itself and methods of handling the material are not easily reproduced. This problem is the source of fluctuations in the properties of the cells as manufactured. If a cell is rejected because its properties fail to meet specifications, it is desirable to recycle the metal cell body. Such recycling is cumbersome, however, because the epoxy present must be removed.

The epoxy may shrink. If it does shrink, leaks and cavities may form, for example, between the metal housing and the epoxy. Leaks may raise detection limits and cavities may cause slow response times. The outgassing and moisture absorption/desorption properties of epoxy are strongly temperature dependent. Consequently the detection limit and response time of an hygrometer containing a material such as epoxy may become temperature dependent.

Any cracking of the glass tube or short circuit of the electrodes inside the glass tube will be difficult to observe directly once the tube is embedded inside epoxy. In addition, epoxy is a relatively expensive material.

Most of the disadvantages and potential causes of malfunctioning listed above as attributable to the use of epoxy in an hygrometer can be discovered only late in the production process. Often discovery occurs indirectly by observing the negative impact of the disadvantages or malfunctions on the performance of the final cell. Moreover, such discovery requires time consuming tests.

SUMMARY OF THE INVENTION

Accordingly, the object of the present invention is to provide an improved electrolytic cell which avoids the use of materials such as epoxy and to provide a method, using such a cell, for the rapid determination of water or moisture in the gas phase. A related object of this invention is to provide a method and apparatus with a low detection limit and to reduce the response time of the electrolytic cell.

Another object is to render the process of manufacturing the electrolytic cell easier, faster, more reproducible, and less expensive. Still another object is to facilitate easy repair of the cell and recycling of the cell body. A reduction in the differential thermal expansion coefficient between the components of the cell is a further object. An additional object is to provide improved components which can be incorporated in existing cells as well as included in new cells.

These objects and advantages are achieved in an electrolytic cell by replacing the conventional epoxy compound with alternative components. The epoxy essentially serves four functions: (1) it mechanically fixes the glass detection unit within the metal housing of the cell; (2) it provides a leak proof barrier between the entrance and exit of the glass tube of the cell, so that the sample gas will flow only through and not around the glass tube; (3) it serves as an electrical insulator for the electrodes; and (4) it provides a leak-tight barrier where the electrical connections penetrate the metal housing of the cell body.

In the present invention, the first two functions are achieved by a compression-type, metal-glass connection seal. Examples of such types of metal-glass connections are O-rings and soft ferrules. Soft ferrules are used, for example, in gas chromatography to connect glass columns to metal tubing. Supelco, Inc., a Rohm and Haas Company, in *Chromatography Products* (Catalog 27 1989), discloses, for example on pages 110–111, commercially available ferrules for connecting glass or metal columns.

An electrical, leak-tight insulator assembly achieves the third and fourth functions in the present invention. That assembly might be a weldable or solderable feedthrough incorporating a ceramic material for electrical insulation. Ceramaseal, a Division of Ceramx, in *Ceramic to Metal Component Catalog* (Catalog 8710 Rev. A 1989), discloses, for example on page A-2, commercially available connectors for providing electrical coupling within ceramic-metal seals.

When combined, the two components--the compression-type, metal-glass connection seal and the electrical, leak-tight insulator assembly--successfully replace the conventional epoxy. Moreover, these components are equally applicable to the conventional electrolytic cell disclosed in U.S. Pat. No. 4,800,000 to D. A. Zatko and to an improved electrolytic cell which incorporates a counterflow geometry.

DESCRIPTION OF THE DRAWINGS

The foregoing and other aspects, features, and advantages of the invention will be apparent from the following description and drawings, in which.

DETAILED DESCRIPTION

Figure 1:
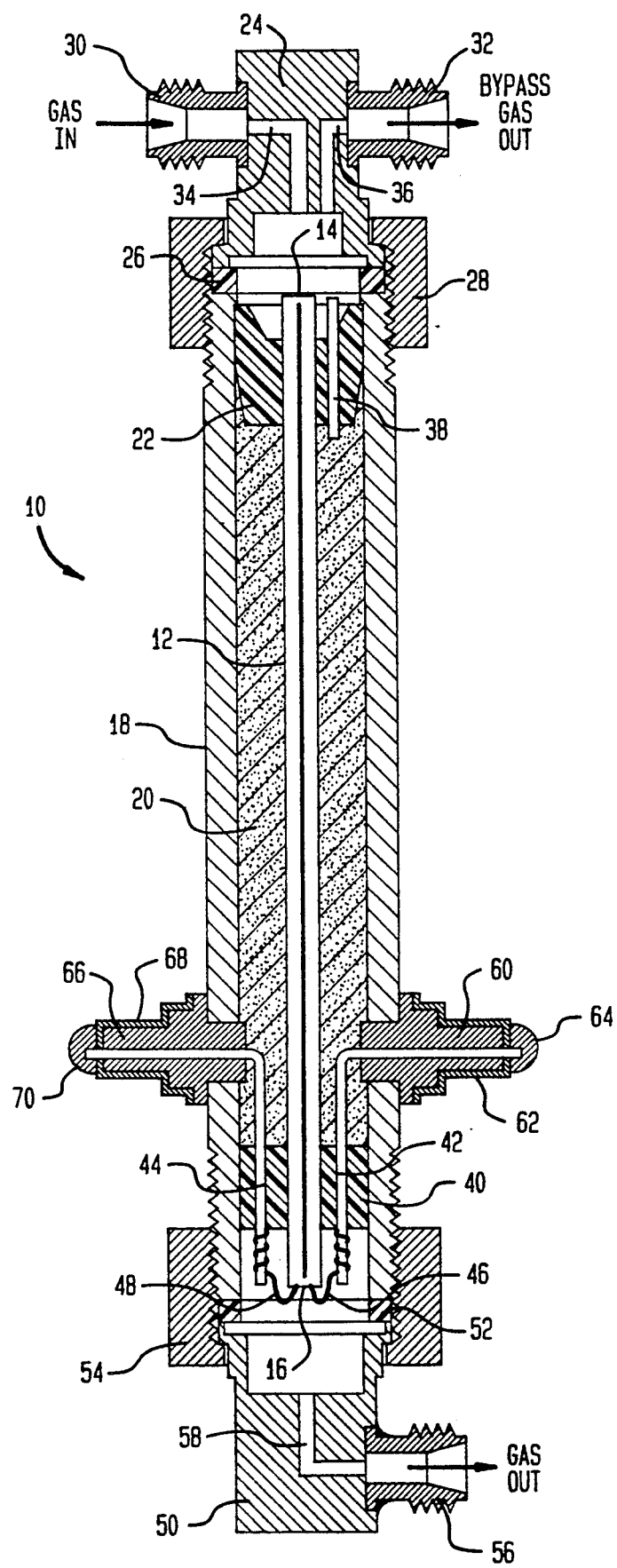
FIG. 1 is a longitudinal cross-sectional view of a conventional electrolytic cell, with epoxy, as disclosed in U.S. Pat. No. 4,800,000 to D. A. Zatko.

Referring now to FIG. 1, an electrolytic cell 10 is known which includes a tubular glass detecting unit 12. Detecting unit 12 passes a gas and has an inlet 14 and an outlet 16. Unit 12 is positioned concentrically in a stainless steel protective housing 18. A packing material 20, typically an epoxy potting compound, fills the concentric area between unit 12 and housing 18.

An inlet plug 22 surrounds and concentrically positions unit 12 at the inlet end of cell 10. An inlet cap 24 is mounted in sealing engagement with a gasket 26 on the upper end of housing 18, and is fixed in position by a nut 28. Arms 30, 32 mounted transversely of cap 24 operate as fittings to attach gas inlet and bypass gas outlet lines, respectively (not shown). Channel 34 conveys gas from fitting 30 through cap 24 to inlet 14 of unit 12. Channel 36 is a bypass conduit connecting cap 24 to fitting 32 to pass gas from a source connected to fitting 30 to a collector connected to fitting 32.

Extending through plug 22 is a tube 38 to admit epoxy 20 during manufacture of cell 10. Tube 38 is plugged upon setting by epoxy 20.

The outlet end of unit 12 is concentrically positioned in housing 18 by plug 40. Electrode leads 42, 44, positioned in plug 40, are connected to the free ends of wires 46, 48 helically covering the interior of unit 12. A bottom cap 50 seats on a gasket 52 and is sealed to and mounted on housing 18 by a nut 54. A gas outlet fitting 56 is mounted in cap 50 as a side arm and receives gas from the interior of cap 50 and unit 12 via a channel 58. Lead 42 extends externally of housing 18 through an electrically insulating packing 60 within a metallic contact arm 62 having a soldered tip 64. Similarly, lead 44 is received in an electrically insulating packing 66 in a metallic contact arm 68 mounted in housing 18 and having a soldered tip 70.

Wires 46, 48 are wound substantially the full length of unit 12 and are exposed to gas passing from inlet 14 to outlet 16. Consequently, all water in the gas passing through detecting unit 12 will be subjected to electrolysis. The interior of unit 12, including wire 46, 48, is coated with a water absorbent film (not shown) which will conduct the ions resulting from electrolysis of the moisture between the two electrodes. The electrolysis current will match the rate at which moisture molecules enter unit 12 when the system has reached equilibrium.

Figure 2:
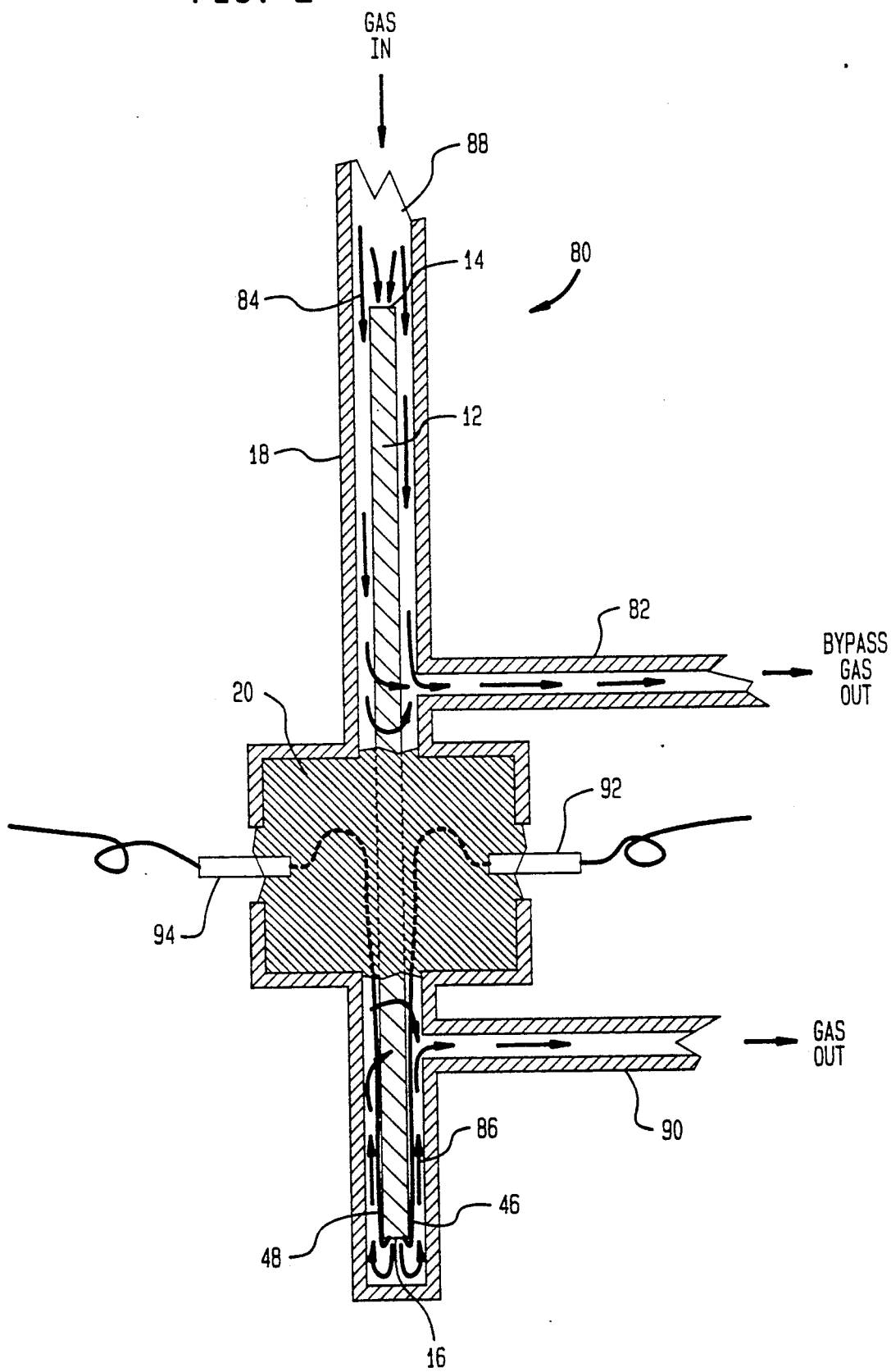
FIG. 2 is a generalized schematic representation of an electrolytic cell incorporating counterflow geometry while using epoxy.

FIG. 2 shows an improvement, the added counterflow features, to the conventional electrolytic cell of FIG. 1. Like reference numbers have been used throughout the various figures to identify like elements.

The electrolytic cell so of FIG. 2 passes a sample gas through a hollow detecting unit 12 so that the gas contacts a moisture absorbent coating (not shown) on the inside surface of unit 12. The absorbed water is electrolyzed and the water concentration determined by measuring the electrical current used in accordance with Faraday's Law. The result of that determination may be manipulated as desired to produce a suitable output reading, e.g. in parts per billion (ppb).

Cell 80 generally includes an entrance 88, an exit 90, a bypass outlet 82, electrode leads 92, 94 and corresponding wires 46, 48, and detecting unit 12 in a suitable housing 18. Unit 12 is typically held in place with epoxy 20 or other material which often has less favorable properties towards outgassing and absorption/desorption of water, causing, respectively, a higher detection limit and a slower response time for cell 80. In cell so, the inlet 14 and outlet 16 of detection means 12 are located upstream in the gas stream at a significant distance from the epoxy or filler level, thereby minimizing the possibility of migration of moisture from this filler level into either the inlet 14 or outlet 16 of unit 12.

The gas flow indicated by the arrows 84 is such that any moisture which is escaping from epoxy 20 must flow against the current of the gas stream in order to reach the inlet 14 of detecting unit 12. Likewise, the output gas shown by the arrows 86 flows in the direction of epoxy 20 before exiting. This counterflow configuration then minimizes the possibility of moisture escaping epoxy 20 or from any other source such as the sample flow exit 90 from entering into the outlet 16 of unit 12. As far as absorption/desorption is concerned, the gas entering unit 12 has not been in contact with epoxy 20, avoiding the slow response time that results from such contact.

As FIG. 2 shows, epoxy 20 provides a leakproof barrier between the gas entering cell 80 at entrance 88 and the gas exiting cell 80 at exit 90. Epoxy 20 also provides an electrical insulator for the electrode leads 92, 94 and corresponding wires 46, 48. Epoxy 20 also provides a leak-tight barrier where the electrode leads 92 and 94 pass through the cell body.

Thus, the improved electrolytic cell 80 incorporates a counterflow geometry to minimize the effects of outgassing and absorption/desorption of water from the materials used to mechanically position the detection unit 12 in the cell, to provide a leak-proof barrier between the entrance 88 and exit 90 of cell 80, to electrically insulate electrode wires 46 and 48 and corresponding electrode leads 92, 94, and to provide a leak-tight barrier where electrode leads 92, 94 pass through the cell housing. The counterflow geometry uses the bypass gas flow and the sample flow exiting the detection unit 12 to prevent a negative influence on the moisture measurement of detection unit 12 by such materials. In the counterflow arrangement, contaminants must flow counter to the bypass and sample gas streams to adversely affect detection. Although an improvement, decreasing contamination and thereby reducing both response time and the low detection limit, even this improved electrolytic cell (shown schematically in FIG. 2) uses an epoxy filler.

Figure 3:
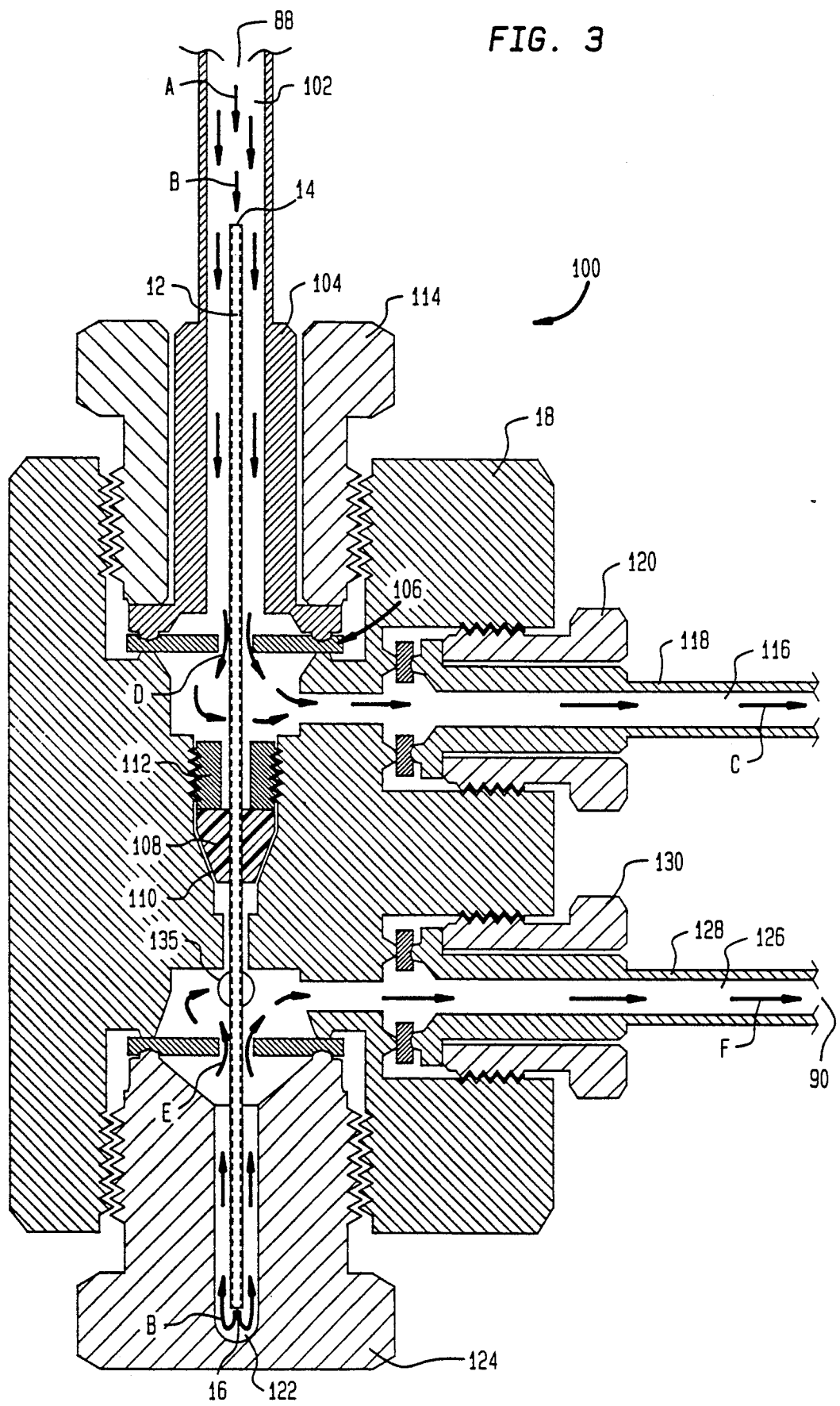
FIG. 3 is a cross-section of an electrolytic cell according to the present invention, adapted for a counterflow geometry, showing the compression-type, glass-metal seal as a soft ferrule and the leak-tight, electrical insulator assembly as weldable, ceramic feedthroughs.
Figure 4:
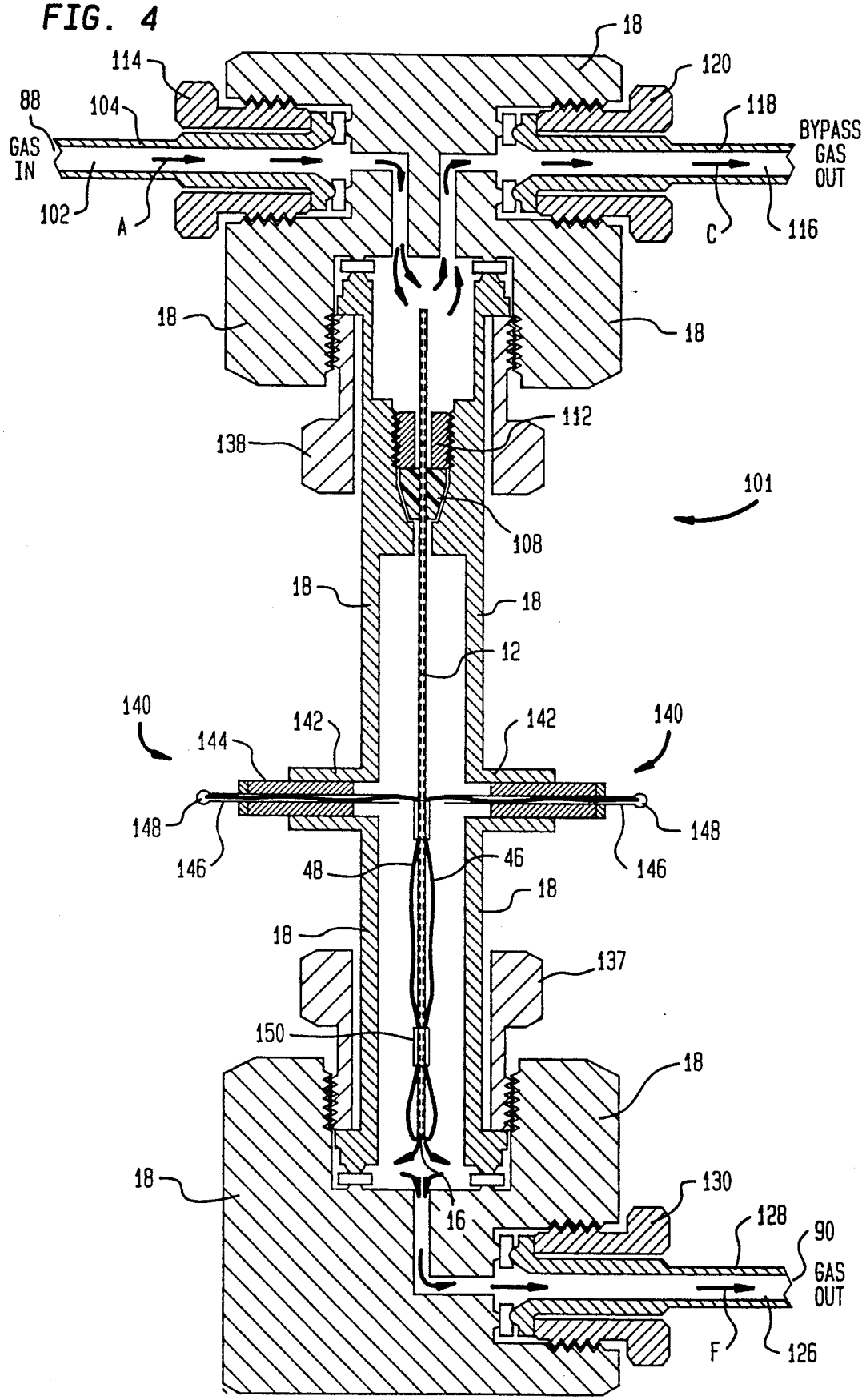
FIG. 4 is a cross-section of an epoxy-less electrolytic cell according to the present invention highlighting the compression-type, glass-metal seal as a soft ferrule and the leak-tight, electrical insulator assembly as weldable, ceramic feedthroughs.

The preferred embodiment of the improved electrolytic cell of the present invention is illustrated in FIGS. 3 and 4, in which the cell is combined, respectively, with and without the counterflow geometry and the additional components are shown which allow a complete removal of the epoxy. Turning first to FIG. 3, the gas to be sampled, designated by arrow A, enters channel 102 formed by tubing 104. Tubing 104 is held in housing 18 by a VCR ® connection 114. As gas A passes down channel 102, it encounters inlet 14 of detecting unit 12. At inlet 14, gas A separates into sample gas B, which passes into unit 12 and is analyzed, and gas D. Rather than enter unit 12, gas D passes between unit 12 and tubing 104.

A VCR ® gasket 106 seals tubing 104 against housing 18. The central opening of gasket 106 and that of the gasket used to connect the plug 124 (discussed below) have a diameter which is minimized to create a locally high speed flow through the narrow passages of the gaskets. Such a flow increases the effectiveness of the counterflow. The diameters of the gaskets are still sufficiently large, however, to pass glass tube 12 and to allow easy installation.

Gas D passes between unit 12 and gasket 106 and, blocked by a compressible seal 108, exits cell 100 as bypass gas C through a channel 116 formed by tubing 118. Tubing 118 is held in housing 18 by a VCR ® connection 120. Any water which might leak from seal 108 must travel upward against the force of gas D to reach inlet 14 and contaminate sample gas B. The force of gas D makes such counterflow difficult, if not impossible; thus, contamination of sample gas B is significantly reduced.

Similarly, a counterflow geometry is provided near outlet 16 to prevent contamination of sample gas B. A cavity 122 formed in the VCR ® plug 124 redirects sample gas B as it exits outlet 16 and creates a counterflow designated by arrow E. The diameter of the central opening in the gasket used to connect plug 124 is sufficiently large both to pass detection unit 12 and to pass the two electrode wires (not shown in FIG. 3) stretched alongside the outside of detection unit 12 without contacting the gasket. Details about the stretched electrode wires are provided in the discussion of FIG. 4.

Counterflow E subsequently leaves cell 100 as exit gas F through a channel 126 formed by tubing 128. Tubing 128 is held in housing 18 by a VCR ® connection 130. Any water which might leak from seal 108 must travel downward against the force of gas E to reach outlet 16 and contaminate sample gas B. The force of gas E makes such counterflow difficult, if not impossible; thus, contamination of sample gas B is significantly reduced.

Seal 108 is preferably a conical-shaped ferrule formed from a soft, compressible material. The shape of seal 108 permits it to engage a frustroconical taper 110 in housing 18. A threaded lock screw 112 having an extra fine thread engages mating threads on housing 18. As screw 112 is screwed into housing 18 it contacts seal 108, exerting a downward force on seal 108 and pressing seal 108 into sealing abutment against taper 110. A horizontal force component is thereby generated, forcing seal 108, which is positioned near the center of detecting unit 12 and surrounds unit 12, to fix unit 12 concentrically within housing 18. Pressed against unit 12 and taper 110, seal 108 also prevents leakage of gas and moisture between entrance 88 and exit 90 of cell 100.

In order to usefully apply the forces generated by the combination of screw 112 and taper 110, seal 108 must be compressible. Seal 108 must be soft so that it secures detecting unit 12, which is usually glass, safely. Suitable materials for seal 108, therefore, include plastics such as Teflon ®. It would be ideal to eliminate all plastics from the high purity gas system. The combination of plastic seal 108, screw 112, and taper 110 with the counterflow geometry approaches, in a practical system, that ideal.

The combination of seal 108, screw 112, and taper 110 could also be used advantageously in the conventional cell 110 illustrated in FIG. 1.

Although the seal 108, screw 112, and taper 110 successfully perform two of the four functions provided by the epoxy 20 of the conventional cell 10 shown in FIG. 1, these components do not execute the third and fourth functions of epoxy 20. The last two functions are providing an electrical insulator for carrying electrode wires 46, 48 and electrode leads 42, 44 to electrical connections (not shown) outside the cell body and providing a leak-tight barrier where electrode leads 42, 44 pass through that cell body. For that purpose, a pair of electrical insulator assemblies 140 are sealingly fixed to housing 18 (see FIG. 4). Insulator assemblies 140 may be horizontally disposed in housing 18 at an axial position denoted by the circle 135 in FIG. 3.

Turning to FIG. 4, an electrolytic cell 101 of the present invention is shown which highlights the electrical insulator assemblies 140. Cell 101 is basically the same as cell 100 shown in FIG. 3 except that no provisions are made to force bypass and sample gas exit flows into a counterflow arrangement. Certain minor changes have been made in FIG. 4 to illustrate that variations in the position of components are feasible. For example, in FIG. 4 cell entrance 88 is horizontal; in FIG. 3, entrance 88 is vertical. An additional VCR ® connection is provided in cell 101 of FIG. 4. FIG. 4 shows electrical insulator assemblies 140 in detail, whereas the insulator assemblies 140 are disposed perpendicular to the plane of FIG. 3 and, hence, are not shown in detail.

In one embodiment of electrical insulator assemblies 140, weld lips 142 are provided to be connected to housing 18. Connections 142 sealingly hold insulating blocks 144, typically made of ceramic. Disposed through the center of insulating blocks 144 are electrical terminals 146, in this case shaped as hollow, metal tubes. Terminals 146 extend from inside housing 18 to outside connections 142 on housing 18. Inside terminals 146, electrode wires 46, 48 are carried from within housing 18 to outside housing 18. Solder 148 closes off, in a leak-tight manner, the ends of terminals 146 and electrically connects electrode wires 46, 48 to those terminals. Thus, electrode wires 46, 48 can be further electrically connected to an external electrical signal receptor.

Wires 46, 48 helically cover the interior of unit 12 until they reach outlet 16 of unit 12. There, once outside unit 12, wires 46, 48 proceed to enter, one each, terminals 146. As shown in FIG. 4, wires 46, 48 may proceed along the outside of unit 12 to reach terminals 146. If so, small, cylindrical pieces of shrink tube 150 may retain wires 46, 48, preventing entanglement of and damage to wires 46, 48 and, in the arrangement as shown in FIG. 3, preventing contact with the gasket.

Electrical insulator assemblies 140 provide an electrical insulator for carrying electrode wires 46, 48 to an external electrical signal receptor (not shown). Assemblies 140 are also sealingly fixed to housing 18. Therefore, electrical assemblies 140 also provide the leak-proof barrier between the gas entering cell 101 at entrance 88 and the gas exiting cell 101 at exit 90.

Additional embodiments for electrical assemblies 140 are possible. For example, the weldable or solderable ceramic assemblies 144 can be replaced by a compression-type connection using a ferrule-shaped insulator. Housing 18 could be provided with a taper to accept such an insulator, and a lock screw could be threaded into housing 18 to compress the insulator—in a manner similar to the arrangement of seal 108. Terminals 146 would then be positioned through the center of the ferrule-shaped insulator.

Although only two arrangements of the present invention are illustrated in FIGS. 3 and 4, it will be recognized that the electrical insulator assemblies 140, the compression-type electrical insulator, and the seal 108, screw 112, and taper 110, could be used with cells (such as that shown schematically in FIG. 2) having counterflow geometry or with conventional cells (such as that shown in FIG. 1).

One advantage of cell 100 and cell 101 over either cell 10 or cell 80 should be highlighted: there is no need to drill out epoxy in order to repair or recycle the cell. Instead, screw 112 is simply removed, providing access to seal 108. Absent the force of screw 112 on seal 108, seal 108 can also be removed or replaced easily.

It will be understood that the foregoing embodiments of the invention are illustrative only and that various changes can be made in the form, details, spatial arrangements, materials, and proportions of the various components of such embodiments without departing from the spirit and scope of the invention as defined by the appended claims.

What is claimed is:

1. An electrolytic cell for the analysis of water in a gas comprising:
   an entrance;
   an exit
   detection means for receiving and measuring water in the gas, said means having an inlet and an outlet for the gas;
   a housing for said detection means; and
   a compressible seal, located a significant distance from said inlet and said outlet of said detecting means, rigidly securing said detection means within said housing, minimizing the amount of epoxy used in said cell, and barring leakage of gas and moisture between said entrance and said exit of said cell through said seal.

2. An electrolytic cell for the analysis of water in a gas comprising:
   detection means for receiving and measuring water in the gas, said means having an inlet and an outlet for the gas and at least one pair of electrode wires for conducting electrical signals from said detection means;
   a housing for said detection means; and
   electrical insulator means sealingly fixed to said housing and having terminals extending from inside said housing to outside said housing, each of said electrode wires being electrically coupled to a respective terminal, said terminals and wires being free of epoxy.

3. An electrolytic cell as claimed in claim 2 further comprising means for rigidly securing said detection means within said housing free of epoxy.

4. An electrolytic cell as claimed in claim 3 wherein said detection means comprises a tubular conduit having said at least one pair of electrically isolated electrode wires helically disposed in parallel on the interior wall of the conduit, said wires covering approximately one-half of the portion of said interior wall exposed to the gas between said inlet and outlet, and a water absorbent coating on said interior wall of said conduit.

5. An electrolytic cell as claimed in claim 4 wherein said securing means is a compressible seal.

6. An electrolytic cell as claimed in claim 5 further comprising means for exerting a vertical force on said compressible seal.

7. An electrolytic cell as claimed in claim 6 wherein said force exerting means is a threaded lock screw.

8. An electrolytic cell as claimed in claim 7 wherein said compressible seal is a soft, conical ferrule and said housing has a frustroconical seat for receiving said seal.

9. An electrolytic cell as claimed in claim 4 wherein said electrical insulator means further comprises:
   connections securing said electrical insulator means to said housing;
   ceramic insulating blocks sealingly held by said connections, said terminals being disposed through said blocks; and
   soldered terminal ends.

10. An electrolytic cell as claimed in claim 9 wherein said electrical insulator means is horizontally disposed in said housing.

11. An electrolytic cell as claimed in claim 9 wherein said connections of said electrical insulator means are welded to said housing.

12. An electrolytic cell as claimed in claim 4 wherein said electrical insulator means comprises compressible, conical ferrules and said housing has frustroconical seats for receiving said ferrules.

13. A process for determining the amount of water in a fluid which comprises passing said fluid through the electrolytic cell of claim 4 so that the water contained in said fluid is absorbed into the coating on said interior wall of said conduit of said cell, electrolyzing said water, and recording the amount of water as a function of the current required to effect said electrolysis.

* * * * *